United States Patent [19]

Gordon et al.

[11] Patent Number: 4,663,125

[45] Date of Patent: May 5, 1987

[54] MEMBRANE MEDICAL DEVICE

[75] Inventors: Timothy M. Gordon, Morrison; Rodger L. Stewart, Lafayette; Daniel J. Wellington, Littleton, all of Colo.

[73] Assignee: Cobe Laboratories, Inc., Lakewood, Colo.

[21] Appl. No.: 735,333

[22] Filed: May 17, 1985

[51] Int. Cl.⁴ .................. A61M 1/14; A61M 1/34
[52] U.S. Cl. .................... 422/48; 422/46; 210/321.4; 210/493.5; 261/DIG. 28
[58] Field of Search .......... 422/46, 48; 210/493.3, 210/493.5, 321.4; 261/DIG. 28

[56] References Cited

U.S. PATENT DOCUMENTS

| | | | |
|---|---|---|---|
| 3,396,849 | 8/1968 | Lande et al. | 422/48 X |
| 3,612,281 | 10/1971 | Leonard | 422/48 X |
| 3,780,870 | 12/1973 | Esmond | 210/321.4 |
| 4,163,721 | 8/1979 | Lobdell | 210/232 |
| 4,219,422 | 8/1980 | Knothe et al. | 422/48 X |
| 4,272,373 | 6/1981 | Stenberg et al. | 210/321.3 X |
| 4,440,722 | 4/1984 | Luppi | 422/46 |
| 4,451,562 | 5/1984 | Elgas et al. | 435/2 |

Primary Examiner—Barry S. Richman
Assistant Examiner—Lynn M. Kummert

[57] ABSTRACT

A perfusion device, such as an oxygenator including a parallel plate membrane consisting of an accordian-folded elongated sheet, is provided with a plurality of perfusion compartments, each with its own inlet and outlet, so that a greater or lesser perfusion membrane area may be used, as desired.

1 Claim, 2 Drawing Figures

MEMBRANE MEDICAL DEVICE

FIELD OF THE INVENTION

This invention relates to perfusion devices, such as oxygenators. More particularly, it relates to such devices in which the overall membrane area is divided into separately accessible portions.

BACKGROUND OF THE INVENTION

It has been known to provide perfusion devices, such as oxygenators, characterized by larger or smaller membrane area and priming volume, for use on patients with larger or smaller blood volume. Pleated membrane perfusion devices are disclosed in Lobdell U.S. Pat. No. 4,163,721, "Edge Sealed Pleated Membrane", granted Aug. 7, 1979, and in Elgas et al. U.S. Pat. No. 4,451,562, "Blood Oxygenator", granted May 29, 1984, both incorporated by reference herein.

SUMMARY OF THE INVENTION

We have discovered that a perfusion device may desirably be provided with separately accessible membrane compartments, so that there may be selectively employed one compartment, or another compartment, or more than one compartment, as desired, for increased flexibility in the volume of blood in a perfusion device in view of unfolding understanding of blood volume, metabolism, and operation conditions.

PREFERRED EMBODIMENT

There is described now a preferred embodiment of the invention.

DRAWINGS

STRUCTURE

Figures 1, 2:
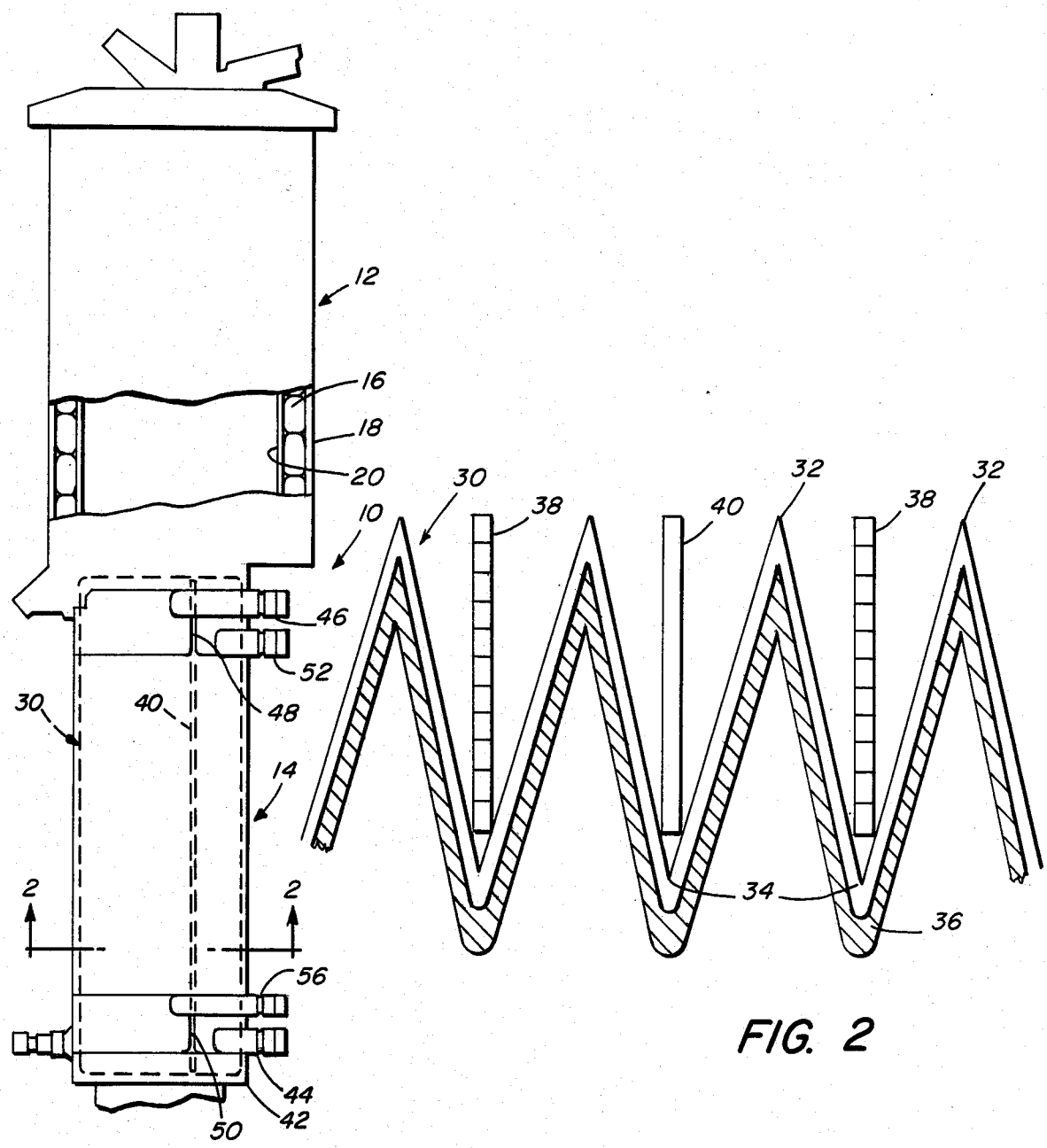
FIG. 1 is a side elevational view, partially in section, of said embodiment.
FIG. 2 is an enlarged, partial, diagrammatic, sectional view, taken at 2—2 of FIG. 1.

Referring now to FIG. 1, there is shown an oxygenator indicated generally at 10. Oxygenator 10 has reservoir portion 12 and oxygenator portion 14. Reservoir portion 12 includes a filter and a defoamer for air separation from venous blood introduced thereinto, as well as turns of heat exchanger tubing 16, wrapped between frustoconical plastic walls 18 and 20.

Extending longitudinally in oxygenator portion 14 is a parallel plate membrane indicated generally at 30, and consisting of an accordion-folded elongated sheet of membrane material; the portions between successive folds 32 and 34 being the "plates". As shown in FIG. 2, interleaved into membrane 30 is an accordion-folded gas side spacer 36. Into the other side of membrane 30 are placed blood side spacer strips 38, except that into one blood side pocket between plates is imperforate plastic fin 40. Both spacer strips 38 and folded spacer 36 are formed of extruded polypropylene netting, through which fluid readily flows, oriented to one another so that ribs on each, at adjacent zones, deform membrane 30 slightly into spaces between pairs of ribs of the other, to improve gas transfer efficiency.

The entire structure shown in FIG. 2 extends from bottom to top of reservoir portion 12, and is sealed thereinto along a bottom portion 42 thereof beneath blood outlet port 44 and along a top portion thereof just above blood inlet port 46.

Fin 40 is aligned with grooves 48 and 50, and located within membrane 30 at a location such that two-thirds of the total membrane area are to the left of the fin, in FIG. 1, and one-third of the total membrane area is to the right thereof. Blood inlet 46 accesses the larger-area (0.85 square meters) left-side portion, and blood inlet 52 accesses the other (0.40 square meters area) portion; blood outlets 56 and 44 respectively serve these two portions.

The gas side of membrane 30 is not compartmentalized.

OPERATION

In operation, perfusion may be accomplished using the 0.85 square meter portion alone, the 0.40 square meter portion alone, or both together to give 1.25 square meters of microporous membrane surface. This gives great flexibility of choice, whether the patient is a large baby or a large adult. It has the further advantage that if volume or metabolic characteristics of the patient are initially misjudged, a shift in the part of the perfusion device that is used may be accommodated during the operation, something particularly facilitated if both compartmented portions are primed initially.

The invention has inventory advantages, decreasing the number of sizes that need be stocked.

Other embodiments within the invention will occur to those skilled in the art.

What is claimed is:

1. A perfusion device comprising
   a housing defining a perfusion region therein,
   an imperforate wall separating said perfusion region into a first membrane zone and a second membrane zone,
   a first pleated membrane section within said first membrane zone, and
   a second pleated membrane section in said second membrane zone,
   wherein said membrane sections are provided by a single pleated membrane sheet and said imperforate wall is interposed into a fold of said membrane sheet to divide said membrane sheet into said first zone and said second zone,
   each said membrane section defining with said housing a fluid flowpath on one side of said membrane section,
   said membrane sections defining with said housing and said wall respective first and second noncommunicating blood flowpaths on the other sides of said membrane sections, said center wall preventing blood flow between said first and second blood flowpaths,
   said housing defining at least one inlet means and one outlet means to said fluid flowpath, a first inlet means and a first outlet means to said first blood flowpath, and a second inlet means and a second outlet means to said second blood flowpath,
   said first and second membrane sections having a different number of membrane folds in them, resulting in said first zone being of a substantially greater capacity than said second zones thereby, permitting three different capacities for said device.

* * * * *

UNITED STATES PATENT AND TRADEMARK OFFICE
CERTIFICATE OF CORRECTION

PATENT NO. : 4,663,125
DATED : May 5, 1987
INVENTOR(S) : Timothy M. Gordon et al.

It is certified that error appears in the above-identified patent and that said Letters Patent are hereby corrected as shown below:

The title "MEMBRANE MEDICAL DEVICE" should be --PERFUSION DEVICE HAVING A PLURALITY OF SEPARATELY ACCESSIBLE MEMBRANE COMPARTMENTS--;

Column 2, line 21, "large baby or a large adult" should be --small baby or a small adult--;

Column 2, line 63, "zones" should be --zone--;

Column 2, line 63, delete ",".

Signed and Sealed this

Eleventh Day of August, 1987

Attest:

DONALD J. QUIGG

Attesting Officer

Commissioner of Patents and Trademarks